(12) United States Patent
Sapper et al.

(10) Patent No.: US 10,145,779 B2
(45) Date of Patent: Dec. 4, 2018

(54) PERTURBED OSCILLATORY KINETICS ELECTROCHEMISTRY SYSTEMS AND METHODS

(71) Applicant: The Boeing Company, Chicago, IL (US)

(72) Inventors: Erik David Sapper, Ballwin, MO (US); Erica Nicole Bilodeau, Danville, CA (US)

(73) Assignee: The Boeing Company, Chicago, IL (US)

( * ) Notice: Subject to any disclaimer, the term of this patent is extended or adjusted under 35 U.S.C. 154(b) by 239 days.

(21) Appl. No.: 15/006,927

(22) Filed: Jan. 26, 2016

(65) Prior Publication Data

US 2017/0212034 A1    Jul. 27, 2017

(51) Int. Cl.
*G01N 17/02* (2006.01)
*G01N 17/04* (2006.01)
*G01N 27/406* (2006.01)

(52) U.S. Cl.
CPC .......... *G01N 17/043* (2013.01); *G01N 17/02* (2013.01); *G01N 27/406* (2013.01)

(58) Field of Classification Search
None
See application file for complete search history.

(56) References Cited

U.S. PATENT DOCUMENTS 5,188,876 A * 2/1993 Hensel .................. E04F 15/02
428/698
5,419,201 A * 5/1995 Li .......................... G01N 3/066
324/71.1
2010/0257642 A1 * 10/2010 Honbo ................... B82Y 35/00
850/1

OTHER PUBLICATIONS

Grendahl (ARL-TR-3099, Dec. 2003).*
Page 80 of Thermal Analysis DMA Q800, Jan. 8, 2011 manual: http://www.tainstruments.com/pdf/brochure/dma.pdf.*
Talonen et al. (Metallurgical and Materials Transactions; Aug. 2004; 35A, 8; p. 2401).*
Man et al. (Procedia Engineering 10, 2011, 1279-1284).*
Mansfeld et al. (Werkstoffe und Korrosion 39, 487-492, 1988).*
Bonora et al. (Werkstoffe und Korrosion 27, 865-870) (Year: 1976).*
"EIS of Organic Coatings and Paints," Gamry Instruments, Inc., Application Note, May 7, 2015.

(Continued)

*Primary Examiner* — Gurpreet Kaur
*Assistant Examiner* — Steven E Rosenwald
(74) *Attorney, Agent, or Firm* — Dascenzo Intellectual Property Law, P.C.

(57) ABSTRACT

Perturbed oscillatory kinetics electrochemistry methods include methods of determining an electrochemical response of a test coupon to a mechanical load. Such methods include applying a cell of electrolyte solution to a test region on a test coupon, contacting the electrolyte solution with a counter electrode, and applying a mechanical load to the test coupon to produce a deflection event. Additionally, methods include measuring a pre-event value of an electrical parameter of the test coupon, before applying the mechanical load, and measuring a post-event value of the electrical parameter, after applying the mechanical load. Methods include determining an electrochemical response of the test coupon to the mechanical load based on the post-event value and the pre-event value.

18 Claims, 3 Drawing Sheets

(56) References Cited

OTHER PUBLICATIONS

"Electrochemistry Accessories," Bio-Logic SAS, Product Catalog, Sep. 2015.
"PTC1™ Paint Test Cell, PortHoles™ Electrochemical Sample Masks," Gamry Instruments, Inc., Aug. 19, 2011.

* cited by examiner

PERTURBED OSCILLATORY KINETICS ELECTROCHEMISTRY SYSTEMS AND METHODS

FIELD

The present disclosure relates to perturbed oscillatory kinetics electrochemistry systems and methods.

BACKGROUND

Corrosion protection may take a variety of forms, including utilizing corrosion-resistant metal alloys, isolating dissimilar metals, applying chemical conversion coatings, plating metals, and applying sealants (e.g., paint, epoxy, polyurethane). Sealants and other surface barriers generally protect the underlying metal from corrosion by isolating the metal from the environment. If the integrity of the surface barrier is compromised, for example, because the barrier does not adhere well to the metal or because the barrier is damaged (cracked, scratched, etc.) or degraded (e.g., weathered), the underlying metal may be exposed to corrosive conditions. Complicating the threat of corrosion due to loss of surface integrity, the underlying structures typically are exposed to stresses that may cause microscopic and/or macroscopic deformations in both the structure and the surface coating. For example, temperature fluctuations may cause expansion and contraction. Further, some structures, like the wing of an aircraft, experience large-scale flexing during ordinary use.

The corrosion protection performance (also referred to as barrier performance) of a coating, a plating, a sealant, or other barrier conventionally is assessed with an accelerated environmental exposure test such as a neutral salt spray test (also referred to as a salt fog test). In a neutral salt spray test, a test sample with a metal substrate is exposed to a spray of a standardized aqueous salt solution and then evaluated for corrosion effects. Some applications may deem corrosion protection performance acceptable when no significant corrosion occurs within 24 hours, 48 hours, 100 hours, 300 hours, 1,000 hours, or longer.

However, accelerated environmental exposure tests such as neutral salt spray tests do not simulate all the stresses experienced by corrosion protection systems. Thus, there exists a need for improved, and/or more comprehensive testing techniques.

SUMMARY

In an aspect, perturbed oscillatory kinetics electrochemistry methods disclosed include methods of determining an electrochemical response of a test coupon to a mechanical load. Such methods include applying a cell of electrolyte solution to a test region on a test coupon, contacting the electrolyte solution with a counter electrode, and applying a mechanical load to the test coupon to produce a deflection event. Additionally, methods include measuring a pre-event value of an electrical parameter of the test coupon, before applying the mechanical load, and measuring a post-event value of the electrical parameter, after applying the mechanical load. Methods include determining an electrochemical response of the test coupon to the mechanical load based on the post-event value to the pre-event value.

In an aspect, perturbed oscillatory kinetics electrochemistry systems disclosed include an apparatus for measuring corrosion protection performance. The apparatus includes a cantilever support configured to support a test coupon at a clamped end, a counter electrode, a reference electrode, a cell configured to hold an electrolyte solution in contact with a test region of the test coupon, a force application mechanism configured to apply a mechanical load to the test coupon at a free end distal to the clamped end, and an electrical meter configured to measure at least one of voltage and electrical current at the test coupon. The counter electrode is configured to electrically contact the test coupon via the cell containing the electrolyte solution. The reference electrode is configured to electrically contact the test coupon and the counter electrode via the cell containing the electrolyte solution. The electrical meter may be configured to measure the voltage or electrical current with one or both of the counter electrode and the reference electrode.

DESCRIPTION

Figure 1:
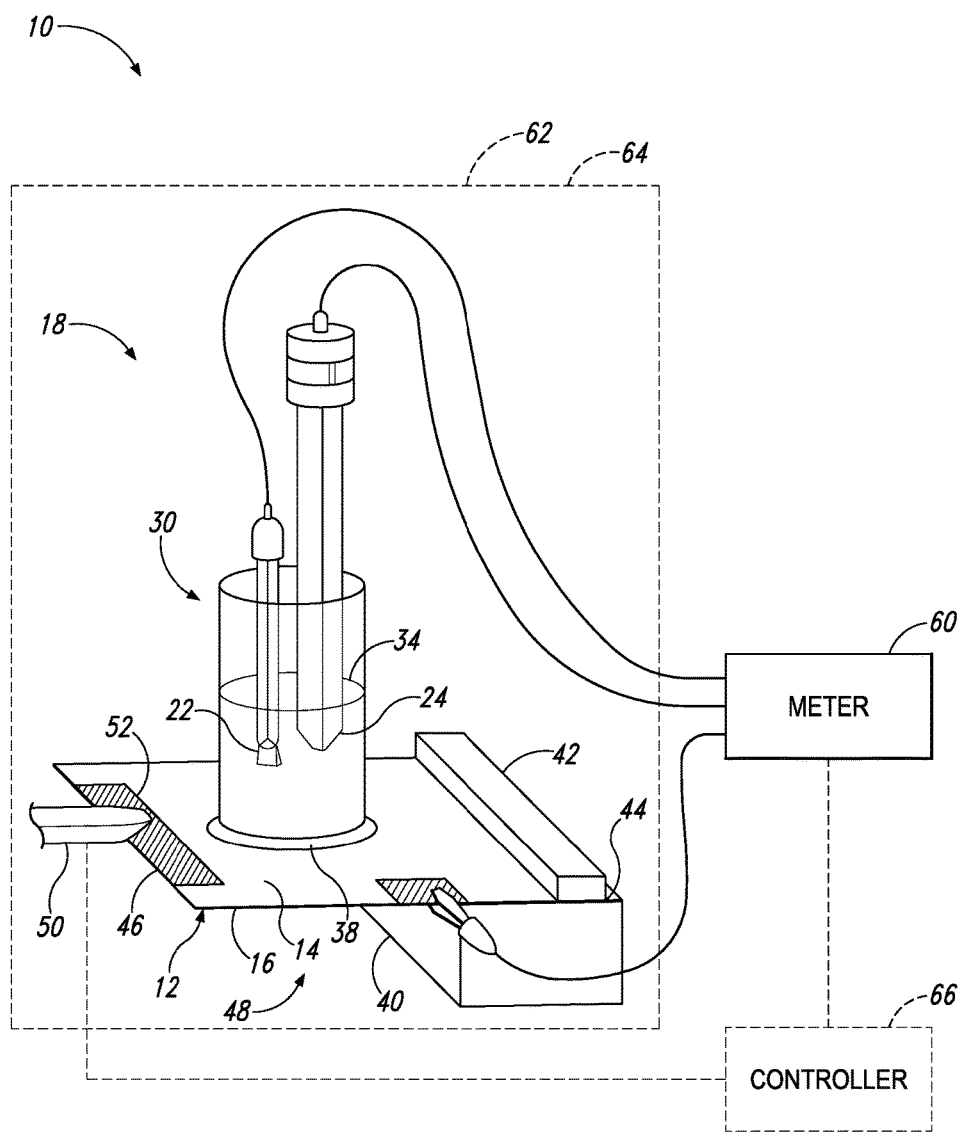
FIG. 1 is a schematic representation of a perturbed oscillatory kinetics electrochemistry system.

The disclosed systems and methods integrate mechanical and electrochemical testing techniques and may be referred to as perturbed oscillatory kinetics electrochemistry (POKE) systems and methods. The POKE systems and methods may be utilized to determine an electrochemical response of a test object to mechanical, electrical, and/or chemical stress. For example, the disclosed systems and methods may be utilized to determine corrosion protection performance and/or barrier performance of coatings. Unless specified otherwise herein, a general reference to coatings or a coating refers to any one or more of chemical conversion coatings, organic coatings, metal plating and other inorganic coatings, sealants, and other moisture or environmental barriers.

With perturbed oscillatory kinetics electrochemistry systems and methods, a test object is subjected to (static and/or dynamic) mechanical loads while being monitored with an electrochemical apparatus for changes in response signal. The test object generally is in the form of a test coupon that includes a metallic, corrodible substrate, and a coating that may protect the substrate from corrosion or exposure to external environments. Generally, the substrate serves as the working electrode. A counter electrode is electrically connected to a cell of electrolyte solution on the test coupon (e.g., on the coating opposite the substrate). The test coupon is subjected to (typically repeating) transient loads that produce deflection events in the test coupon. A transient load is a mechanical load resulting from a force applied to the test coupon. The deflection event caused by the transient load is a mechanical response of the test coupon to the transient load. As discussed further herein, the deflection event may be static or dynamic, and may include deflection, deformation, and/or distortion. The applied transient loads perturb the test coupon, subjecting the substrate, the coating, and the interface between the substrate and coating to (typically oscillatory) stress. The mechanical stresses of the deflection events represent mechanical stresses potentially encountered by coatings and coated objects deployed in environmental conditions, for example, mechanical stresses due to thermal fluctuations, and/or use of the coated object (resulting from significant and/or variable forces). The deflection events may cause degradation, material fatigue, and/or discernable physical, chemical, or geometric/volumetric changes in the coating, the substrate, and the interface between the substrate and coating.

Because of the sensitivity of the electrochemistry technique integrated into the perturbed oscillatory kinetics electrochemistry technique, tests may be performed for relatively short periods of time, e.g., minutes or hours, rather than the long periods of time associated with conventional environmental tests such as salt fog tests. Degradation, potentially even nascent degradation, may be indicated by changes in electrochemical properties of the test setup. For example, the capacitance of a test coupon may be used to characterize the quality of a coating. High quality coatings, with few or no defects, and which seal the underlying substrate, typically exhibit a low capacitance and a high impedance. Lower quality or degraded coatings may have water infiltration and thus a higher capacitance and/or lower impedance. Hence, a test coupon subject to transient loads may exhibit an increase in capacitance as the coating degrades, with the character of the increase (amount, rate, etc.) related to the corrosion protection performance, or decrease in such. Higher quality coating-substrate combinations may be selected based upon the corrosion protection performance indicated by the perturbed oscillatory kinetics electrochemistry technique.

FIGS. 1-4 relate to perturbed oscillatory kinetics electrochemistry systems and methods. In general, in the drawings, elements that are likely to be included in a given example are illustrated in solid lines, while elements that are optional or alternatives are illustrated in dashed lines. However, elements that are illustrated in solid lines are not essential to all examples of the present disclosure, and an element shown in solid lines may be omitted from a particular example without departing from the scope of the present disclosure. Elements that serve a similar, or at least substantially similar, purpose are labelled with numbers consistent among the figures. Like numbers in each of the figures, and the corresponding elements, may not be discussed in detail herein with reference to each of the figures. Similarly, all elements may not be labelled or shown in each of the figures, but reference numerals associated therewith may be used for consistency. Elements, components, and/or features that are discussed with reference to one or more of the figures may be included in and/or used with any of the figures without departing from the scope of the present disclosure.

FIG. 1 illustrates a perturbed oscillatory kinetics electrochemistry system 10, also referred to as a POKE system 10 and a system 10. The system 10 includes and/or is configured to operate with a test coupon 12. The test coupon 12 may be a sample produced for the purpose of testing and/or may be a component or whole apparatus. Hence, the test coupon 12 may be referred to as a test object, a test sample, a test component, and/or a test apparatus. The test coupon 12 is generally flat and/or sheet-like, and/or may include a flat and/or sheet-like region. The test coupon 12 may be a laminate and/or layered structure including a substrate 16 and an optional coating 14. The test coupon 12 (e.g., the substrate 16 and/or the coating 14) is probed with an electrochemical measurement apparatus 18, typically a three-electrode setup with a working electrode 20, counter electrode 22, and a reference electrode 24. In some examples, the measurement apparatus 18 includes no reference electrode 24 (e.g., only a working electrode 20 and a counter electrode 22). The measurement apparatus 18 includes the test coupon 12 and/or is configured to probe the test coupon 12.

The working electrode 20 is an electrode associated with the test coupon 12. The term 'working electrode' is used in analog to conventional electrochemical systems. However, the working electrode 20 is not necessarily the electrode where a reaction of interest, or any other reaction, occurs. The working electrode 20 is not necessarily oxidized or reduced. The working electrode 20 is not necessarily more or less reactive than the counter electrode 22. The working electrode 20 may have a standard electrode potential greater than, less than, or substantially equal to the standard electrode potential of the counter electrode 22. The working electrode 20 may be anodic or cathodic.

Similarly, the counter electrode 22 is an electrode associated with a cell 30 of electrolyte solution 34 coupled to the test coupon 12 (as discussed further herein). The counter electrode 22 operates counter to the working electrode 20, i.e., the counter electrode 22 serves as a cathode when the working electrode 20 serves as an anode and vice versa. The term 'counter electrode' is used in analog to conventional electrochemical systems. However, the counter electrode 22 is not necessarily more or less reactive than the working electrode 20. The counter electrode 22 may have a greater, lesser, or substantially equal surface area as the working electrode 20. The counter electrode 22 may be oxidized or reduced, anodic or cathodic. In some examples, substantially no electrical current passes between the working electrode 20 and the counter electrode 22 (e.g., the electrical resistance between them is greater than 1 MΩ (megaohm), greater than 10 MΩ, greater than 100 MΩ, or greater than 1 GΩ (gigaohm)). Additionally or alternatively, substantially no reaction occurs at either electrode. In some examples, the counter electrode 22 has a greater surface area than the working electrode 20, and/or reactions (typically corrosion reactions) at the working electrode 20 limit the electrochemical process. In some examples, the counter electrode 22 may include and/or may be at least substantially constructed of electrochemically inert materials such as gold, platinum, or carbon. Electrochemically inert materials generally transfer electrons rather than exchange ions into solution. Electrochemically inert materials may be used to avoid releasing undesired ions into solution and/or to avoid undesired electrochemical reactions at the counter electrode 22.

The test coupon 12 includes the working electrode 20, an electrically conductive element. Generally, the working electrode 20 is the substrate 16. For example, the test coupon 12 and/or the substrate 16 may include, may be constructed of, and/or may be substantially metal such as structural metals that may be subjected to environmental exposure (e.g., steel, aluminum, titanium, and/or alloys thereof). Further, the test coupon 12 and/or the substrate 16 may include, may be constructed of, and/or may be substantially a conductive material such as carbon fiber and/or conductive polymers. Additionally or alternatively, the working electrode 20 may be an electrode embedded in and/or coupled to the body of the test coupon 12. The electrode embedded in and/or coupled to the body of the test coupon 12 may be at least substantially constructed of conventional electrochemical electrode materials such as platinum, gold, carbon, copper, silver, etc.

Test coupon 12 may include the coating 14. If present, the coating 14 contacts the substrate 16 and covers the substrate 16 in at least a region of the surface of the test coupon 12 (i.e., coating 14 forms at least a portion of the outer surface of the test coupon 12). For example, coating 14 may be bonded to, adhered to, and/or coated on substrate 16. Coating 14 generally is non-conductive, insulative, and/or dielectric (e.g., coating 14 may form a dielectric barrier over the substrate 16). In some examples, coating 14 may be conductive (e.g., coating 14 may be a metal plating). The thickness of coating 14 is relatively thin, i.e., generally thinner than the substrate 16. For example, the thickness of coating 14 may be at least 0.01 μm (microns), at least 1 μm, at least 10 μm, at least 100 μm, at most 5 mm (millimeters), at most 1 mm, at most 100 μm, and/or at most 10 μm. Thinner coatings 14 may have fewer defects (more likely to be defect free), while thicker coatings 14 may provide more mechanical, electrical, and/or thermal protection to the underlying substrate 16. Coating 14 may be a multilayer system that includes individual coating layers as described. Hence, coating 14 may include one or more coating layers with each layer being at least one of a chemical conversion coating, organic coating, metal plating or other inorganic coating, sealant, or other moisture or environmental barrier. In some examples, the test coupon 12 may include and/or may be a 'bare' substrate 16, having no coating 14.

Substrate 16 may be electrically conductive or non-conductive, and may include surface oxidization, contamination, or other surface layers that may deter or enhance corrosion or other surface reactions. When present, the surface layers of the substrate 16 may be under the coating 14. Substrate 16 generally forms the bulk of the test coupon 12 and typically is a structural layer of the test coupon 12. Test coupon 12 and/or substrate 16 generally are thin (having a sheet-like form with a thickness substantially smaller than lateral dimensions), with a thickness of at most 100 mm, at most 20 mm, at most 10 mm, at most 5 mm, at least 0.5 mm, at least 1 mm, and/or at least 5 mm. The other (lateral) dimensions of the test coupon 12 may be at least 20 mm, at least 50 mm, at least 100 mm, at most 1000 mm, and/or at most 500 mm. The thickness of test coupon 12 and/or substrate 16 generally corresponds to the thickness of the structures which are mimicked by the test coupon 12 and/or the substrate 16. In some examples, test coupon 12 and/or substrate 16 are thin (and/or thinner than the mimicked structures) to facilitate application of mechanical loads sufficient to cause deflection events. For example, the dimensions of test coupon 12 and/or substrate 16 may be configured to exhibit deflection events under relatively small mechanical loads (e.g., less than 300 N (Newtons) or less than 100 N).

Coupled to a region of the test coupon 12 is a cell 30 of electrolyte solution 34. The cell 30 is a container for the electrolyte solution 34 and has at least one open end that is closed by the test coupon 12. The cell 30 may include, and/or may be, a tube, capillary, bottle, and/or vessel with one or more open ends. At least one of the open ends of the cell 30 is applied to the test coupon 12 about a test region 36 of the test coupon 12. The test region 36 is a surface region of the test coupon 12 and may include a portion of the coating 14 and/or the substrate 16. Hence, the cell 30 is configured to hold electrolyte solution 34 in contact with the test region 36, e.g., the coating 14 and/or the substrate 16. The cell 30 is at least partially filled with the electrolyte solution 34 to contact the test region 36. Having an open end which is not closed by the test coupon 12 may facilitate filling the cell 30 and/or inserting the counter electrode 22 and the optional reference electrode 24. The electrolyte solution 34 is an electrically conductive solution, typically an aqueous solution. Electrolyte solutions 34 generally include ionic components of an acid, a base, and/or a salt.

The measurement apparatus 18 includes the cell 30, optionally with the electrolyte solution 34.

The cell 30 may be chemically inert (e.g., configured to chemically withstand the electrolyte solution 34 and non-reactive with the electrodes) and electrically insulating (e.g., configured to avoid leakage currents outside of the electrolyte solution 34). For example, the cell 30 may include, and/or may be at least substantially constructed of, glass and/or plastic (such as polyethylene, polypropylene, polycarbonate, etc.).

The cell 30 may be fluidically sealed to the test coupon 12 about the test region 36 to contain the electrolyte solution 34 in contact with the test region 36 and/or to substantially prevent leakage of the electrolyte solution 34. The cell 30 may be sealed with a seal 38, which may include sealant, adhesive, bonding agent, etc., and/or which may include a gasket, O-ring, etc. The cell 30 may be sealed, and/or the seal 38 may be configured, to withstand the mechanical stress applied to the test coupon 12 (as discussed further herein). Further, the seal 38 may be chemically inert and/or configured to chemically withstand the electrolyte solution. The seal 38 may include, and/or may be at least substantially constructed of, silicone, silicone adhesive, epoxy, rubber, synthetic rubber, etc.

With the cell 30 applied to the test coupon 12 and the counter electrode 22 in contact with the electrolyte solution 34 in the cell 30, the test coupon 12 (e.g., the substrate 16) may serve as the working electrode 20 to the counter electrode 22, with at least the electrolyte solution 34 separating the electrodes. Alternatively stated, the counter electrode 22 electrically contacts the test coupon 12 (e.g., the coating 14 and/or the substrate 16) via the cell 30 containing the electrolyte solution 34. Generally, the cell 30 is applied to the coating 14 of the test coupon 12 so that the coating 14 generally separates the electrolyte solution 34 from the substrate 16.

Measurement apparatus 18 of system 10 may include a reference electrode 24 configured to contact and/or in contact with the electrolyte solution 34 in the cell 30. Thus, the reference electrode 24 may be in electrical contact with the test coupon 12 and the counter electrode 22 via the electrolyte solution 34. The reference electrode 24 typically has a constant absolute electrochemical potential provided that the electrical current through the reference electrode 24 is sufficiently low (e.g., less than 1 nA (nanoampere)). The reference electrode 24 may be a conventional electrochemical reference electrode such as a standard hydrogen electrode, a normal hydrogen electrode, a saturated calomel electrode, and a silver/silver chloride electrode.

Measurement apparatus 18 and/or system 10 are configured to perform one or more electroanalytical techniques and may include a two-electrode setup (the working electrode 20 and the counter electrode 22), a three-electrode setup (the working electrode 20, the counter electrode 22, and the reference electrode 24), and/or a multi-electrode setup (including at least one working electrode 20, at least one counter electrode 22, and at least one reference electrode 24). The working electrode 20 and the counter electrode 22 operate to supply electrical current across the electrolyte solution 34, the coating 14, and/or the substrate 16. In some measurements, the voltage of the counter electrode 22 is permitted to react to the current supplied (sourced or sinked) by the counter electrode 22. Hence, the voltage of the working electrode 20 typically is measured relative to the reference electrode 24, which has a stable voltage and which does not supply much, if any, current.

As noted herein, the working electrode 20 may be the substrate 16 or other conductive element of the test coupon 12. The working electrode 20 may be electrically connected to an electrical meter 60 via a lead that contacts a working electrode site 56 of the test coupon 12. The working electrode site 56 may include a bare conductive surface that is a portion of the working electrode 20 (e.g., a portion of the substrate 16 without coating 14) and/or that is in electrical contact with the working electrode 20.

System 10 includes an electrical meter 60 to measure electrical parameters between the working electrode 20, the counter electrode 22, and/or the reference electrode 24. The measurement apparatus 18 may include electrical meter 60. The electrical meter 60 generally measures electrical parameters such as voltage, electrical current, electric charge, and/or related electrical parameters (e.g., resistance, capacitance, impedance, open-circuit potential, power, electrochemical noise, etc.). Measured electrical parameters may be steady-state values, frequency dependent values, and/or statistical measures such as average value, standard deviation, average deviation, and root mean squared deviation. Examples of electrical meters 60 include an electrometer, a potentiostat (including bipotentiostats and polypotentiostats), a galvanostat, a voltmeter, an ammeter, an ohmmeter, a multimeter, an electrochemical impedance spectroscopy (EIS) analyzer, a frequency response analyzer (FRA), and a spectrum analyzer. Electrical meters 60 may be configured to apply a voltage to one or more of the electrodes (and/or across two or more of the electrodes) and/or to supply current from one or more of the electrodes (and/or between two or more of the electrodes). Hence, electrical meters 60 may include a voltage source and/or a current source. As used herein, electrical meters 60 are not limited to three-electrode devices and may be two-electrode devices, three-electrode devices, four-electrode devices, and/or multi-electrode devices. Electrical meters 60 are configured, adapted, and/or selected for compatibility with the number and kind of electrodes in system 10 (specifically the working electrode(s) 20, the counter electrode(s) 22, and the optional reference electrode(s) 24).

The electrical meter 60 may be configured to control the voltage difference between the working electrode 20 and one or both of the counter electrode 22 and the reference electrode 24 (e.g., the reference electrode 24 may be the same element as the counter electrode 22). The voltage difference may be controlled by supplying current through the counter electrode 22. The current supplied by the electrical meter 60 between the counter electrode 22 and the working electrode 20 may be measured or otherwise determined by the electrical meter 60. Thus, the electrical meter 60 may be configured substantially as a potentiostat (controlling voltage and measuring current). Additionally or alternatively, the electrical meter 60 may be configured to control the current between the working electrode 20 and the counter electrode 22. The current may be controlled by applying a voltage to the counter electrode 22 and/or the working electrode 20. The voltage applied by the electrical meter 60 to the counter electrode 22 and/or the working electrode 20 may be measured or otherwise determined by the electrical meter 60 (e.g., measuring the voltage between the counter electrode 22 and the working electrode 20, and/or measuring the voltage between the reference electrode 24 and the working electrode 20). Thus, the electrical meter 60 may be configured substantially as a galvanostat (controlling current and measuring voltage). In some examples, the electrical meter 60 is configured to apply a voltage difference of substantially zero (a short circuit) between the two controlled electrodes (measuring the current generated by the electrodes) and/or configured to supply a current of substantially zero (an open circuit) between the two controlled electrodes (measuring the voltage generated by the electrodes).

Measurement apparatus 18 of system 10 is configured to hold the test coupon 12 in a cantilever arrangement with a clamped end 44 of the test coupon 12 secured to a support 40 and a free end 46 of the test coupon 12 (distal to the clamped end 44) held out over an overhang region 48 without any direct underlying support (such as a vertical support). The cantilever arrangement may facilitate application of the mechanical load in the overhang region 48 (e.g., at the free end 46) and induction of a deflection event in the overhang region 48, as discussed further herein. Though described in terms of over and under, the overhang region 48 and/or the test coupon 12 are not necessarily oriented to withstand the effects of gravity at the free end 46. The overhang region 48 and/or the test coupon 12 may be oriented substantially horizontally (as generally illustrated in FIG. 1), substantially vertically, or at some angle between horizontal and vertical. Further, the test coupon 12 is not necessarily substantially planar or characterized by any orientation in a single plane.

Measurement apparatus 18 may include one or more supports 40, also referred to as cantilever supports, and/or one or more clamps 42 configured to clamp the clamped end 44 of the test coupon 12. The support 40 may support the test coupon 12 vertically, horizontally, or in any other orientation. The clamped end 44 and the clamp(s) 42 may be electrically isolated from each other. One or both of the clamped end 44 and the clamp(s) 42 may include an insulating layer and/or barrier configured to electrically isolate the test coupon 12 from the clamps 42.

The test region 36 is arranged to experience a deflection event induced by a mechanical load (a force) applied to a load contact site 52 on the test coupon 12. The load contact site 52 (also referred to as the contact site and/or the force application site) is configured to accept application of the mechanical load to the test coupon 12. The load contact site 52 may be configured for abrasion resistance, electrical isolation, and/or thermal isolation. The load contact site 52 is arranged to induce the deflection event at the test region 36 (e.g., the load contact site 52 is proximate and/or adjoining the test region 36 with little to no intervening barriers). The load contact site 52 is generally in the overhang region 48, and/or spaced away from the clamped end 44, to facilitate application of the mechanical load and induction of the deflection event. The load contact site 52 may be at the free end 46, between the free end 46 and the clamped end 44, between the free end 46 and the cell 30 (and/or the test region 36), and/or between the clamped end 44 and the cell 30 (and/or the test region 36). The test region 36 (and the cell 30) generally is in the overhang region 48, and/or spaced away from the clamped end 44, to facilitate reception of the deflection event. The test region 36 (and the cell 30) may be at the free end 46 or between the free end 46 and the clamped end 44.

Conventional electrochemical systems and/or apparatuses typically are configured to avoid mechanical and/or electrical disturbances applied to the corresponding test coupon because such disturbances can obscure the measurement of electrochemical effects occurring at the test coupon. Mechanical and/or electrical disturbances to a conventional electrochemical system may induce electrical noise with a magnitude at least as great as the typical electrical signals (typical electrical signals may have an intensity of 1-100 nanowatts). Contrary to conventional electrochemical system design, system 10 is configured to accept a mechanical load applied to the test coupon 12 and to measure the response of the test coupon 12 to the applied mechanical load. System 10 is configured to accept the mechanical load applied to the load contact site 52 and to permit the applied mechanical load to induce a deflection event at the test region 36.

System 10 may include a force application mechanism 50 configured to apply a mechanical load to the test coupon 12 at the load contact site 52. Measurement apparatus 18 may include the force application mechanism 50. The force application mechanism 50 is configured to impart the mechanical load to the test coupon 12 and to thereby induce a deflection event in the test coupon 12. The force application mechanism 50 may be configured, arranged, shaped, and/or selected to contact the load contact site 52.

The force application mechanism 50 may be automated and/or manually operated. Further, system 10 may be configured to permit direct application of a load to the test coupon 12 by an operator (e.g., by tapping the load contact site 52 with one's finger). A force application mechanism 50 (automated and/or manually operated) may provide for repeatable application of mechanical loads and/or application of mechanical loads of predetermined magnitudes. Further, the force application mechanism 50 may be configured, adapted, and/or selected to simulate an anticipated mechanical stress to the structure that the test coupon 12 mimics. The force application mechanism 50 may include a striker, a hammer, a tooth, a prong, and/or an actuator configured to contact the load contact site 52 and/or to impart the mechanical load to the test coupon 12. For example, the force application mechanism 50 may include a weight to drop from a fixed height, the weight striking the load contact site 52 and/or operating a striker to strike the load contact site 52. As another example, the force application mechanism 50 may include a lever, gear, and/or cam configured to press the load contact site 52 as the lever, gear, and/or cam changes position.

The force application mechanism 50 is configured to induce a deflection event at the test region 36. The deflection event is due to generally elastic deflection, deformation, and/or distortion of the load contact site 52 and/or the test region 36. The deflection event includes a deflection phase when a force is applied to the load contact site 52 and may include a release phase after the force is removed from the contact site 52 (i.e., after the force ceases and/or ceases to be applied). Thus, the deflection event may include dynamic deflection and/or static deflection (e.g., deflection to achieve equilibrium and/or quasi-equilibrium). The deflection event may include oscillatory motion and/or dampened motion. The force application mechanism 50 may be configured to apply a single deflection event and/or to apply a series (e.g., a periodic series) of deflection events to the test coupon 12. Each deflection event may impart a similar amount of force and/or energy to the test coupon 12 (e.g., a repeatable force and/or energy). Additionally or alternatively, the force application mechanism 50 may be configured to impart different amounts of force and/or energy for different deflection events.

System 10 may include an electromagnetic interference (EMI) shield 62 to isolate the test coupon 12 and/or the measurement apparatus 18 from the external environment (e.g., from electromagnetic fields in the external environment). The EMI shield 62 may be configured to shield the test coupon 12, the working electrode 20, the cell 30 of electrolyte solution 34, the counter electrode 22 contacting the electrolyte solution 34, and the optional reference electrode 24 contacting the electrolyte solution 34. Moreover, the EMI shield 62 may be configured to shield the support 40, the clamp 42, the electrical meter 60, and/or the force application mechanism 50. The EMI shield 62 may include passive and/or dynamic attenuation of external electromagnetic fields. For example, the EMI shield 62 may include an electrical conductor, a magnetic shield, a Faraday cage, a cloak, etc. Shielded and/or attenuated electromagnetic frequencies may include radio frequencies and/or microwave frequencies. The EMI shield 62 may surround and/or enclose the shielded components.

System 10 may include a vibration control system 64 to isolate the test coupon 12 and/or the measurement apparatus 18 from the external environment (e.g., from external vibrational energy such as sound, infra-sound, and motion). The vibration control system 64 may be configured to isolate the test coupon 12, the working electrode 20, the cell 30 of electrolyte solution 34, the counter electrode 22 contacting the electrolyte solution 34, and the optional reference electrode 24 contacting the electrolyte solution 34. Moreover, the vibration control system 64 may be configured to isolate the support 40, the clamp 42, the electrical meter 60, and/or the force application mechanism 50. The vibration control system 64 may include passive and/or dynamic attenuation of external mechanical energy. For example, the vibration control system 64 may include a vibration isolation table, a dampened spring, and/or a sound isolation enclosure. Controlled and/or attenuated vibrational frequencies may include greater than 0.1 Hz (Hertz), greater than 0.5 Hz, greater than 1 Hz, less than 1000 Hz, less than 100 Hz, and/or less than 10 Hz.

System 10 may include a controller 66. The controller 66 may be configured, adapted, and/or programmed to acquire electrical parameter values with the electrical meter 60 (e.g., values associated with the working electrode 20, the counter electrode 22, and/or the reference electrode 24) and/or to apply voltages and/or electrical currents with the electrical meter 60. The controller 66 may be configured, adapted, and/or programmed to operate the force application mechanism 50, the clamp 42, the EMI shield 62, and/or the vibration control system 64. Generally, the controller 66 is configured to coordinate acquisition of electrical parameter values via the electrical meter 60 and operation of the force application mechanism 50, and/or to control the system 10 as a whole. The controller 66 may be configured, adapted, and/or programmed to perform any of the methods disclosed herein. The controller 66 includes (and/or may be) a computing device and may be referred to as a microcontroller, an embedded controller, and/or an embedded system. As used herein, where the controller 66 is configured, adapted, and/or programmed to perform a function, the configuration, adaptation, and/or programming may be in the form of hardware (e.g., wiring, digital logic chips), firmware (e.g., field-programmable gate array, embedded code), and/or software.

Figure 2:
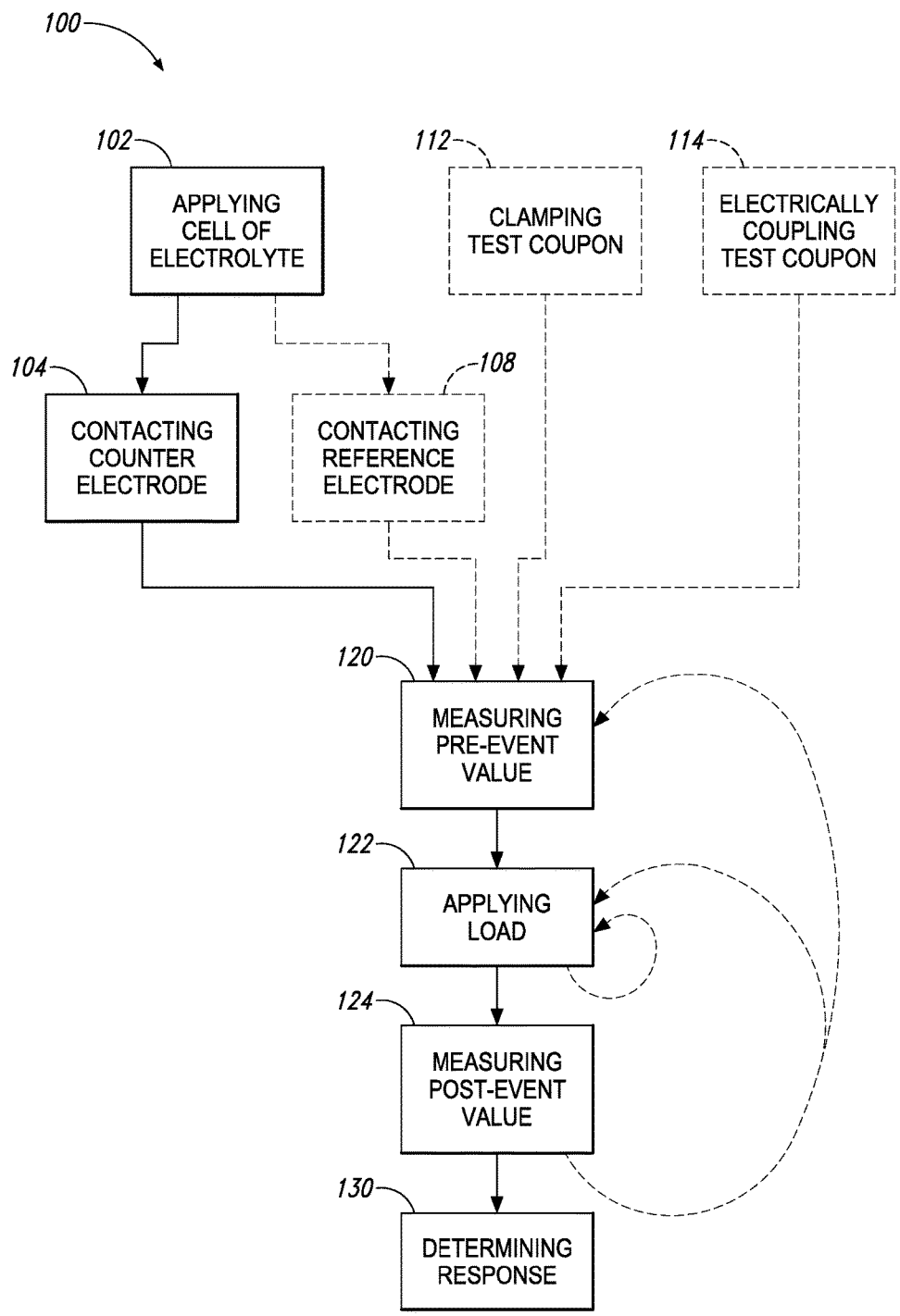
FIG. 2 is a schematic representation of perturbed oscillatory kinetics electrochemistry methods.

FIG. 2 illustrates methods 100 according to the present disclosure. Methods 100 may include determining an electrochemical response of a test object such as a test coupon (e.g., test coupon 12), assessing electrochemical response of a test object to mechanical stress, and/or assessing corrosion protection performance of one or more coating-substrate combinations. Methods 100 may be performed with the system 10 and/or the measurement apparatus 18 (both shown in FIG. 1).

Methods 100 include applying 102 a cell of electrolyte solution to a test region on a test coupon, contacting 104 the electrolyte solution with a counter electrode, and applying 122 a mechanical load to the test coupon to produce a deflection event. Further, methods 100 include measuring 120 a pre-event value of an electrical parameter of the test coupon before applying 122 the mechanical load and measuring 124 a post-event value of the electrical parameter after applying 122 the mechanical load. Methods 100 may include contacting 108 the electrolyte solution with a reference electrode, clamping 112 the test coupon in a cantilevered arrangement, electrically coupling 114 at least a portion of the test coupon as a working electrode, and/or determining 130 an electrochemical response of the test coupon to the mechanical load based on the pre-event value and the post-event value.

The electrical parameter may be the voltage of the test coupon and/or the working electrode (that is part of the test coupon) relative to the counter electrode and/or the reference electrode in contact with the electrolyte solution. Moreover, the electrical parameter may be the electrical current between the test coupon (and/or the working electrode) and the counter electrode. Further, the electrical parameter may be a parameter related to the voltage, electrical current and/or electrical charge at the test coupon and/or working electrode (e.g., open-circuit potential, electrical power, noise, etc.), and/or a property (e.g., resistance, capacitance, impedance, etc.) of the test coupon and/or components thereof (e.g., an electrical property such as resistance, capacitance, or impedance, and/or a non-electrical property such as volume, porosity, density, length, etc.). The electrical parameter may include any of the described parameters and/or properties, in which case the electrical parameter may be a derived parameter that depends at least in part on the underlying parameter. For example, the electrical parameter may be a statistical measure of an underlying parameter such as an average value, a standard deviation, an average deviation, and/or a root mean squared deviation.

Applying 122 the mechanical load includes producing a deflection event as described herein. For example, the deflection event may include an application phase while the mechanical load is applied and an optional release phase after the mechanical load is removed (i.e., after the mechanical load ceases and/or ceases to be applied). Applying 122 the mechanical load may include inducing a deflection at the test region and/or inducing oscillatory motion and/or dampened motion at the test region. Applying 122 the mechanical load may include applying the mechanical load to a load contact site of the test coupon (e.g., the load contact site 52). The mechanical load may be transient, e.g., an impulsive load.

Applying 122 the mechanical load may include repeatedly applying mechanical loads, e.g., applying a series of mechanical loads, to produce deflection events, e.g., a series of deflection events. The mechanical loads may be applied (and/or the deflection events may occur) in groups and/or periodically. Applying 122 may include applying (and/or producing) at least 2, at least 5, at least 10, at least 20, at most 100, at most 50, and/or at most 20 mechanical loads (and/or deflection events). Repeated applying 122 and/or deflection events may be performed at regular or irregular intervals of, e.g., at least 0.2 seconds, at least 1 second, at least 5 seconds, at most 500 seconds, at most 100 seconds, and/or at most 20 seconds. The interval between repeated mechanical loads and/or deflection events may be selected to separate the deflection events in time, e.g., avoiding complete overlap, substantial overlap, and/or significant overlap.

Measuring 120 and measuring 124 may be performed with the measurement apparatus 18 and/or the electrical meter 60. Measuring 120 and measuring 124 may be performed using conventional techniques associated with a two-electrode setup, a three-electrode setup, and/or a multi-electrode setup. Measuring 120 and measuring 124 may include potentiometry, voltammetry, amperometry, and/or coulometry, any of which may be static and/or dynamic (e.g., measuring a steady state and/or a frequency dependent quantity). Measuring may include measuring the same or related parameters with a witness apparatus which does not experience mechanical loads and corresponding deflection events. Measuring the witness apparatus may include measuring the test coupon 12 before, after, and/or between applications of mechanical loads. The witness apparatus may include a substantially similar test coupon and test equipment as the measurement apparatus 18. The witness apparatus may be a positive control, a negative control, and/or a baseline. For example, the witness apparatus may include a test coupon with a coating with a known integrity (e.g., sealed or breached).

Methods 100 may include repeatedly applying 122 the mechanical load (or loads) and then measuring 124 the post-event value after applying the mechanical load (or loads). The repeating may be in groups and/or periodically. The measuring 124 the post-event value may be performed synchronously with the applying 122 the mechanical load. For example, the application of a mechanical load may be followed by a measurement of the post-event value that occurs a predefined period of time after the application of the mechanical load. A series of application and measurement cycles may be performed with the predefined period of time substantially the same for each cycle. As indicated in FIG. 2, a measurement cycle may include measuring 120 a pre-event value, one or more applying 122 the mechanical load, and/or measuring 124 the post-event value. Each measurement cycle includes at least one applying 122 and at least one of measuring 120 and measuring 124. Measurement cycles, individual measuring 120, and/or individual measuring 124 may be repeated in one or more groups of at least 2, at least 5, at least 10, at least 20, at most 100, at most 50, and/or at most 20.

Figure 3:
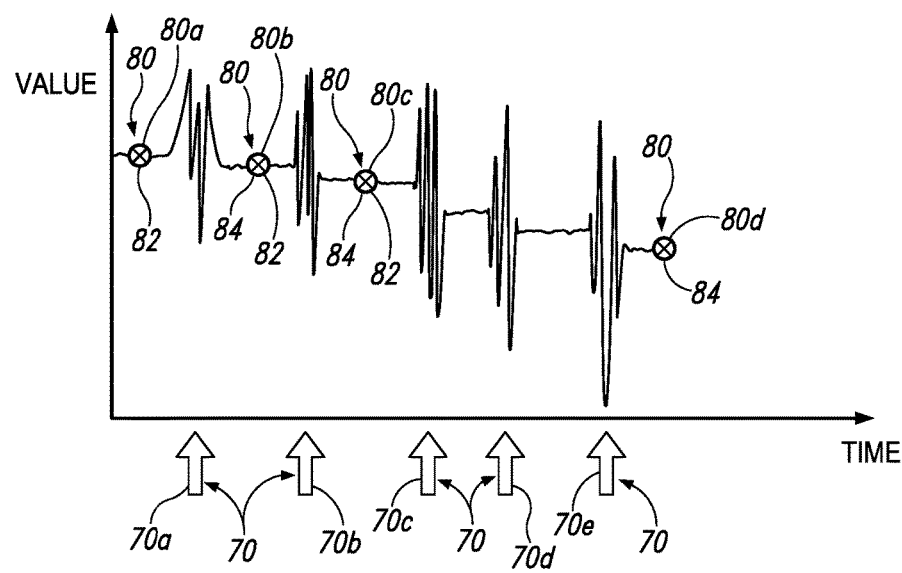
FIG. 3 is a schematic representation of an electrical parameter response to deflection events.
Figure 4:
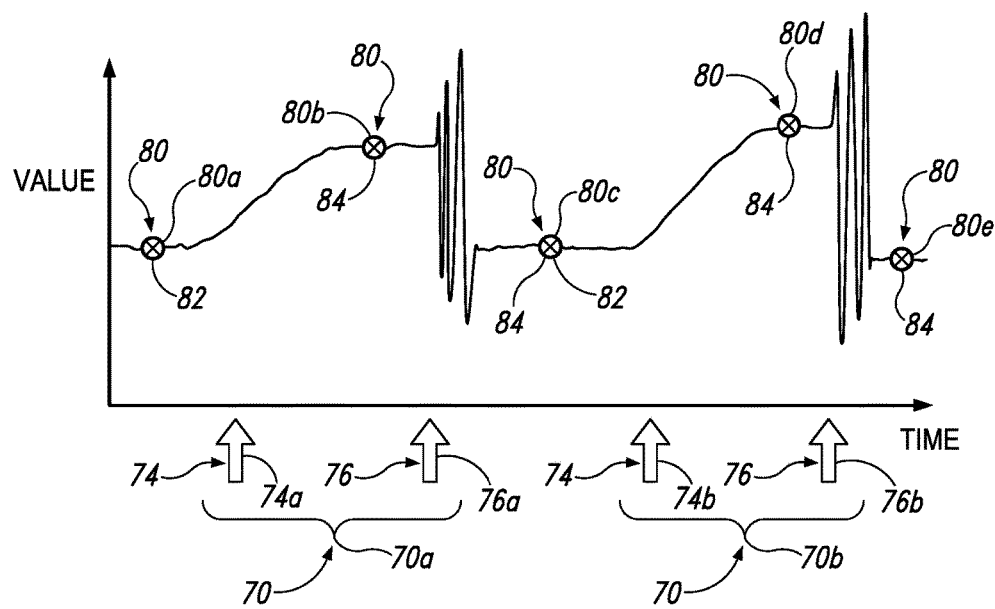
FIG. 4 is a schematic representation of an electrical parameter response to application of a load and removal of the load.

Measuring 120 and measuring 124 are primarily distinguished in that measuring 120 includes measuring a pre-event value before a deflection event while measuring 124 includes measuring a post-event value upon and/or after a deflection event. Where deflection events are repeatedly induced, the post-event value for one deflection event may be the same as the pre-event value for the next deflection event. For example, FIG. 3 schematically represents the value of an electrical parameter as a function of time. Deflection events 70 (induced by applying 122 the mechanical load) may cause the value to oscillate, become noisy, and/or become essentially unmeasurable. Between deflection events 70, one or more values 80 may be measured. In FIGS. 3 and 4, individual deflection events 70 and measured values 80 are respectively denoted 70a, 70b, 70c, etc. and 80a, 80b, 80c, etc. In FIG. 3, the earliest measured value 80a is also a pre-event value 82 because it is measured prior to the first deflection event 70a. That is, the earliest measured value 80a is the result of measuring 120 the pre-event value 82 prior to applying 122 the mechanical load. The next measured value 80b is after the first deflection event 70a and so may be called a post-event value 84 relative to the first deflection event 70a. Additionally, the same measured value 80b is prior to the second deflection event 70b and so may be called a pre-event value 82 relative to the second deflection event 70*b*. A repeated series of applications of mechanical loads and the resulting deflection events 70 (as shown in FIG. 3) includes at least one measured value 80 measured before one of the deflection events 70 and at least one measured value 80 measured during and/or after one of the deflection events 70. Between deflection events 70, zero, one, two, or more values 80 may be measured.

Measuring 124 a post-event value 84 may be performed upon the applying 122 the mechanical load, triggered by the applying 122, during the deflection event, a predefined time after the deflection event starts and/or stops, and/or at a time determined by the deflection event. For example, FIG. 4 illustrates deflection events 70 that include an application phase 74 in which the mechanical load is applied and a release phase 76 in which the mechanical load is removed. Application phases 74 and release phases 76 also are labelled with letters corresponding to the individual deflection event (e.g., deflection event 70*a* includes application phase 74*a* and release phase 76*a*). In the example of FIG. 4, the application phase 74 includes applying the mechanical load and permitting the test coupon to achieve a quasi-equilibrium (e.g., a steady state) in response to the applied load. The electrical parameter has an initial measured value 80*a* (the first pre-event value 82) that increases upon application of the mechanical load and eventually plateaus at a new measured value 80*b* (the first post-event value 84, before the first release phase 76*a*). The measured value 80*b* may be measured a predefined time after the start of the application phase 74*a* and/or after the value of the electrical parameter is sufficiently stable (e.g., by monitoring the electrical parameter value until the measurement noise is low enough to achieve a desired measurement precision, e.g., a precision sufficient to distinguish the measured values 80*a*, 80*b*, 80*c*, etc.).

The release phase 76 may cause the electrical parameter to oscillate, become noisy, and/or become essentially unmeasurable. In some instances, the release phase 76 may induce a smooth transition of the electrical parameter to a new value and/or may permit continued measurement of the electrical parameter. Hence, measuring 124 the post-event value 84 may occur during and/or immediately after the release phase 76. Measuring 124 the post-event value 84 may include measuring a quantity related to the value during and/or immediately after the application phase 74 and/or the release phase 76, even in instances where the value of the electrical parameter is oscillating rapidly, noisy, and/or essentially unmeasurable. For example, the integrated value during and/or after the corresponding application phase 74 and/or release phase 76 may be measured. Additionally or alternatively, the value of the electrical parameter may be low pass filtered prior to measuring.

As illustrated in FIGS. 3-4, the measured value 80 may change after one or more induced deflection events 70. The response of the measured value 80 with respect to the number, intensity, duration, and/or character of deflection events 70 may indicate the integrity of the test coupon and/or the coating of the test coupon. As the integrity of the test coupon and/or the coating are related to the corrosion protection performance, the response of the measured value 80 may indicate the corrosion protection performance. For instance, the magnitude, duration, and/or character (e.g., slope, integral, noise) of the measured values 80 may be used to characterize the relative corrosion protection performance of different test coupons and/or different combinations of coatings and substrates. As an example, the (relative or absolute) magnitude of capacitance change of a coating with respect to a given number of deflection events may be used to indicate corrosion performance. As another example, the number of deflection events required to produce a given capacitance change (relative or absolute) may be used to indicate corrosion performance. A corrosion performance indicator may include and/or may be the magnitude, duration, and/or character of the response of measured values 80 of one or more electrical parameters with respect to the number, intensity, duration, and/or character of the applied mechanical loads and/or the induced deflection events 70.

Returning generally to FIG. 2, determining 130 the electrochemical response may include determining the corrosion performance indicator, the response of the electrical parameter measured by the measuring 120 and measuring 124, and/or an indicator related to the measured values 80. The electrical parameters and/or the measured values 80 may be used as a proxy for, and/or converted to, derived electrical parameters, derived electrochemical response variables, non-electrical properties, and the like. For example, the open circuit potential may indicate the electrochemical accessibility of the working electrode and the integrity of the coating of the test coupon covering the working electrode. As another example, non-electrical properties of the test coupon may be derived from electrical parameters and/or electrochemical response variables through the use of equivalent circuit modeling, parameter fitting, comparative analysis, or other methods of evaluation.

Determining 130 the electrochemical response may be performed after a given time, a given number of applied mechanical loads, a given number of measured values 80, and/or after a predetermined change in measured values 80. For example, determining 130 may include determining the electrochemical response based upon at least 2, at least 5, at least 10, at least 20, at most 100, at most 50, and/or at most 20 measured values 80. Determining 130 may include calculating a difference, sum, product, ratio, average, standard deviation, and/or other mathematical function of two or more measured values 80.

Applying 102 the cell of electrolyte solution to the test region on the test coupon may include arranging the cell of electrolyte solution as described herein with respect to cell 30, electrolyte solution 34, and test region 36. Applying 102 may include positioning the cell at the test region, sealing the cell at the test region, and/or at least partially filling the cell with electrolyte solution.

Clamping 112 the test coupon may include clamping the test coupon in a cantilevered arrangement with a clamped end of the test coupon clamped to a support (e.g., support 40) and a free end of the test coupon distal to the clamped end. The clamped end, the free end, and the test region may be arranged as described herein with respect to clamped end 44, free end 46, and test region 36. Clamping 112 may include vertically supporting the test coupon at the clamped end or supporting the test coupon in any other orientation. Clamping 112 may include holding the free end and the test region over an overhang region (e.g., the overhang region 48) without an underlying support.

Methods 100 may include electrically isolating the test coupon from the external environment (e.g., external electromagnetic fields). Electrical interference and noise from the external environment may influence the measurement process, potentially biasing or obscuring the electrical parameter to be measured. Electrically isolating may include isolating the measurement apparatus (e.g., measurement apparatus 18). Electrically isolating may include actively and/or passively attenuating electromagnetic fields, e.g., shielding the test coupon and/or the measurement apparatus with an EMI shield (e.g., EMI shield 62). Electrically isolating may include attenuating electromagnetic fields at radio frequencies and/or microwave frequencies. Electrically isolating may include surrounding and/or enclosing the test coupon and/or the measurement apparatus with the EMI shield.

Methods 100 may include vibrationally isolating the test coupon from the external environment (e.g., from external mechanical and/or vibrational energy). Mechanical interference and noise from the external environment may influence the measurement process, potentially mimicking and/or inducing deflection events. Vibrationally isolating may include isolating the measurement apparatus (e.g., measurement apparatus 18). Vibrationally isolating may include actively and/or passively attenuating external mechanical and/or vibrational energy, e.g., isolating the text coupon and/or the measurement apparatus with a vibration control system (e.g., vibration control system 64). Vibrationally isolating may include attenuating 'natural' and/or resonant frequencies of the support apparatus for the test coupon and/or the measurement apparatus. Vibrationally isolating may include attenuating a vibration frequency of greater than 0.1 Hz, greater than 0.5 Hz, greater than 1 Hz, less than 1000 Hz, less than 100 Hz, and/or less than 10 Hz. Vibrationally isolating may include surrounding and/or enclosing the test coupon and/or the measurement apparatus with a sound isolation enclosure.

Examples of inventive subject matter according to the present disclosure are described in the following enumerated paragraphs.

A1. A method of determining an electrochemical response of a test coupon, the method comprising:

applying a cell of electrolyte solution to a test region on a test coupon;

contacting the electrolyte solution with a counter electrode;

applying a mechanical load to the test coupon to produce a deflection event;

before applying the mechanical load, measuring a pre-event value of an electrical parameter of the test coupon;

after applying the mechanical load, measuring a post-event value of the electrical parameter; and determining an electrochemical response of the test coupon to the mechanical load based on the post-event value and the pre-event value.

A1.1. The method of paragraph A1, wherein the measuring the pre-event value includes measuring the pre-event value with the counter electrode.

A1.2. The method of any of paragraphs A1-A1.1, wherein the measuring the post-event value includes measuring the post-event value with the counter electrode.

A2. The method of any of paragraphs A1-A1.2, further comprising clamping the test coupon in a cantilevered arrangement with a clamped end of the test coupon clamped to a cantilever support and a free end of the test coupon distal to the clamped end.

A2.1. The method of paragraph A2, wherein the test region is between the clamped end and the free end.

A2.2. The method of paragraph A2, wherein the test region is at the free end.

A2.3. The method of any of paragraphs A2-A2.2, wherein the clamping includes vertically supporting the test coupon at the clamped end.

A2.4. The method of any of paragraphs A2-A2.3, wherein the clamping includes holding the free end and the test region over an overhang region without a vertical support.

A3. The method of any of paragraphs A1-A2.4, wherein the applying the mechanical load includes applying the mechanical load to a contact site of the test coupon.

A3.1. The method of paragraph A3, wherein the contact site is at an end of the test coupon, optionally at a/the free end of the test coupon.

A3.2. The method of any of paragraphs A3-A3.1, wherein the contact site is between a/the clamped end of the test coupon and a/the free end of the test coupon.

A3.3. The method of any of paragraphs A3-A3.2, wherein the contact site is between the test region and a/the clamped end of the test coupon.

A4. The method of any of paragraphs A1-A3.3, wherein the deflection event includes an application phase while the mechanical load is applied and a release phase after the mechanical load is removed.

A5. The method of any of paragraphs A1-A4, wherein the applying the mechanical load includes applying a series of mechanical loads to produce a series of deflection events, optionally wherein the series of deflection events is greater than 2, greater than 5, greater than 10, greater than 20, less than 100, less than 50, and/or less than 20 deflection events.

A6. The method of any of paragraphs A1-A5, wherein the applying the mechanical load includes inducing a dampened oscillatory motion of the test region.

A7. The method of any of paragraphs A1-A6, wherein the mechanical load is a transient mechanical load.

A8. The method of any of paragraphs A1-A7, further comprising repeating applying the mechanical load and then measuring the post-event value after applying the mechanical load.

A8.1. The method of paragraph A8, wherein the applying the mechanical load and the measuring the post-event value are performed synchronously.

A8.2. The method of any of paragraphs A8-A8.1, wherein the repeating is performed periodically.

A9. The method of any of paragraphs A1-A8.2, wherein the electrical parameter includes at least one of voltage between the counter electrode and the test coupon, electrical current between the counter electrode and the test coupon, capacitance between the counter electrode and the test coupon, resistance between the counter electrode and the test coupon, impedance between the counter electrode and the test coupon, capacitance of the test coupon in the test region, resistance of the test coupon in the test region, impedance of the test coupon in the test region, and open-circuit potential between the counter electrode and the test coupon in the test region.

A10. The method of any of paragraphs A1-A9, wherein the determining the electrochemical response includes determining a corrosion performance indicator based on the pre-event value and the post-event value.

A10.1. The method of paragraph A10, wherein the corrosion performance indicator includes at least one of a difference of and a ratio of the pre-event value and the post-event value.

A11. The method of any of paragraphs A1-A10.1, further comprising vibrationally isolating the test coupon from an external environment and optionally from external vibrational energy.

A11.1. The method of paragraph A11, wherein the vibrationally isolating includes vibrationally isolating a measurement apparatus that includes the test coupon, the cell of electrolyte solution, the counter electrode contacting the electrolyte solution, the optional reference electrode contacting the electrolyte solution, and the optional cantilever support.

A11.2. The method of any of paragraphs A11-A11.1, wherein the vibrationally isolating includes supporting the test coupon and/or a/the measurement apparatus that includes the test coupon with a vibration isolation table.

A11.3. The method of any of paragraphs A11-A11.2, wherein the vibrationally isolating includes substantially surrounding the test coupon and/or a/the measurement apparatus that includes the test coupon with a sound isolation enclosure.

A11.4. The method of any of paragraphs A11-A11.3, wherein the vibrationally isolating includes attenuating an environmental vibration frequency of greater than 0.1 Hz, greater than 0.5 Hz, greater than 1 Hz, less than 1000 Hz, less than 100 Hz, and/or less than 10 Hz.

A12. The method of any of paragraphs A1-A11.4, further comprising electrically isolating the test coupon from an/the external environment and optionally from external electromagnetic fields.

A12.1. The method of paragraph A12, wherein the electrically isolating includes electrically isolating a/the measurement apparatus that includes the test coupon, the cell of electrolyte solution, the counter electrode contacting the electrolyte solution, the optional reference electrode contacting the electrolyte solution, and the optional cantilever support.

A12.2. The method of any of paragraphs A12-A12.1, wherein the electrically isolating includes surrounding the test coupon and/or a/the measurement apparatus including the test coupon with a Faraday cage.

A12.3. The method of any of paragraphs A12-A12.2, wherein the electrically isolating includes attenuating at least one of radio-frequency electromagnetic fields and microwave-frequency electromagnetic fields.

A13. The method of any of paragraphs A1-A12.3, wherein the test coupon includes a substrate.

A13.1. The method of paragraph A13, wherein the test coupon includes a coating that covers at least a portion of the substrate.

A13.1.1. The method of paragraph A13.1, wherein the coating is between the substrate and the electrolyte solution in the test region.

A13.1.2. The method of any of paragraphs A13.1-A13.1.1, wherein the coating forms a dielectric barrier over the substrate in the test region.

A13.1.3. The method of any of paragraphs A13.1-A13.1.2, wherein the coating is at least one of an insulative coating, a dielectric coating, a sealant, and a moisture barrier.

A13.2. The method of any of paragraphs A13-A13.1.3, wherein the substrate is at least one of a conductive substrate and a metal substrate.

A13.3. The method of any of paragraphs A13-A13.2, wherein the substrate is electrically connected as a working electrode to the counter electrode.

A14. The method of any of paragraphs A1-A13.3, wherein the test coupon is at least one of a panel, a sheet, and a laminate.

A15. The method of any of paragraphs A1-A14, wherein the applying the cell includes sealing, optionally flexibly sealing, the cell to the test coupon about the test region, optionally with a gasket.

A15.1. The method of paragraph A15, wherein the test coupon includes at least one of a coating and a substrate, and wherein the applying the cell includes sealing the cell to at least one of the coating and the substrate.

A16. The method of any of paragraphs A1-A15.1, further comprising contacting the test coupon with the electrolyte solution within the cell.

A16.1. The method of paragraph A16, wherein the test coupon includes at least one of a coating and a substrate, and wherein the contacting the test coupon with the electrolyte solution includes contacting at least one of the coating and the substrate with the electrolyte solution.

A17. The method of any of paragraphs A1-A16.1, further comprising electrically coupling the test coupon as a working electrode, the counter electrode, and an optional reference electrode to an electrical meter, and optionally wherein the electrical meter is at least one of a potentiostat, a galvanostat, and an electrometer.

A18. The method of any of paragraphs A1-A17, wherein the test coupon serves as a working electrode and wherein the measuring the pre-event value and the measuring the post-event value include measuring an electrical current between the counter electrode and the working electrode while maintaining a voltage between the counter electrode and the working electrode.

A19. The method of any of paragraphs A1-A18, wherein the test coupon serves as a working electrode and wherein the measuring the pre-event value and the measuring the post-event value include measuring a voltage between the counter electrode and the working electrode while maintaining an electrical current between the counter electrode and the working electrode, and optionally wherein the electrical current is zero.

A20. The method of any of paragraphs A1-A19, further comprising contacting the electrolyte solution with a reference electrode.

A20.1. The method of paragraph A20, wherein the test coupon serves as a working electrode and wherein the measuring the pre-event value and the measuring the post-event value include measuring an electrical current between the counter electrode and the working electrode while maintaining a voltage between the reference electrode and the working electrode.

A20.2. The method of any of paragraphs A20-A20.1, wherein the test coupon serves as a working electrode and wherein the measuring the pre-event value and the measuring the post-event value include measuring a voltage between the reference electrode and the working electrode while maintaining an electrical current between the counter electrode and the working electrode, and optionally wherein the electrical current is zero.

A20.3. The method of any of paragraphs A20-A20.2, wherein the measuring the pre-event value includes measuring the pre-event value with the reference electrode.

A20.4. The method of any of paragraphs A20-A20.3, wherein the measuring the post-event value includes measuring the post-event value with the reference electrode.

A20.5. The method of any of paragraphs A20-A20.4, wherein the electrical parameter includes the open-circuit potential between the reference electrode and the test coupon in the test region.

A21. The method of any of paragraphs A1-A20.5, wherein the method is a method of assessing corrosion protection performance of a coating on a metal substrate.

A22. The method of any of paragraphs A1-A21, wherein the method is a method of assessing electrochemical response to mechanical stress.

B1. An apparatus for measuring corrosion protection performance, the apparatus comprising:
a cantilever support configured to support a test coupon at a clamped end;
a counter electrode;
a cell configured to hold an electrolyte solution in contact with a test region of the test coupon, and wherein the counter electrode is configured to electrically contact the test coupon via the cell containing the electrolyte solution;
a force application mechanism configured to apply a mechanical load to the test coupon at a free end distal to the clamped end; and
an electrical meter configured to measure at least one of voltage and electrical current at the test coupon.

B2. The apparatus of paragraph B1, wherein the force application mechanism is configured to apply to the test coupon at least one of a repeatable force, a repeated force, and a periodic force.

B3. The apparatus of any of paragraphs B1-B2, wherein the force application mechanism is configured to produce a deflection event on the test coupon.

B4. The apparatus of any of paragraphs B1-B3, wherein the force application mechanism is configured to deflect the test coupon and then release the test coupon.

B5. The apparatus of any of paragraphs B1-B4, wherein the force application mechanism includes one or more of a striker, a hammer, a tooth, a prong, and an actuator.

B6. The apparatus of any of paragraphs B1-B5, wherein the electrical meter is at least one of a potentiostat, a galvanostat, and an electrometer.

B7. The apparatus of any of paragraphs B1-B6, wherein the electrical meter is configured to measure at least one of voltage between the counter electrode and the test coupon, electrical current between the counter electrode and the test coupon, capacitance between the counter electrode and the test coupon, resistance between the counter electrode and the test coupon, impedance between the counter electrode and the test coupon, capacitance of the test coupon in the test region, resistance of the test coupon in the test region, impedance of the test coupon in the test region, and open-circuit potential between the counter electrode and the test coupon in the test region.

B8. The apparatus of any of paragraphs B1-B7, wherein the counter electrode includes at least one of platinum, gold and carbon.

B9. The apparatus of any of paragraphs B1-B8, further comprising a reference electrode configured to electrically contact the test coupon and the counter electrode via the cell containing the electrolyte solution.

B9.1. The apparatus of paragraph B9, wherein the reference electrode is one of a standard hydrogen electrode, a normal hydrogen electrode, a saturated calomel electrode, and a silver/silver chloride electrode.

B9.2. The apparatus of any of paragraphs B9-B9.1, wherein the electrical meter is configured to measure voltage between the reference electrode and the test coupon.

B10. The apparatus of any of paragraphs B1-B9.2, further comprising a vibration isolation system to isolate the test coupon and/or a measurement apparatus that includes the test coupon from an external environment and optionally from external vibrational energy.

B10.1. The apparatus of paragraph B10, wherein the measurement apparatus includes the test coupon, the cell, the cantilever support, the counter electrode, the force application mechanism, and the optional reference electrode.

B10.2. The apparatus of any of paragraphs B10-B10.1, wherein the vibration isolation system includes at least one of a vibration isolation table, a dampened spring, and a sound isolation enclosure.

B10.3. The apparatus of any of paragraphs B10-B10.2, wherein the vibration isolation system is configured to attenuate an environmental vibration frequency of greater than 0.1 Hz, greater than 0.5 Hz, greater than 1 Hz, less than 1000 Hz, less than 100 Hz, and/or less than 10 Hz.

B11. The apparatus of any of paragraphs B1-B10.3, further comprising an electromagnetic interference shield to isolate the test coupon and/or a measurement apparatus that includes the test coupon from an/the external environment and optionally from electromagnetic fields.

B11.1. The apparatus of paragraph B11, wherein the measurement apparatus includes the test coupon, the cell, the cantilever support, the counter electrode, the force application mechanism, and the optional reference electrode.

B11.2. The apparatus of any of paragraphs B11-611.1, wherein the electromagnetic interference shield includes a Faraday cage.

B11.3. The apparatus of any of paragraphs B11-611.2, wherein the electromagnetic interference shield is configured to attenuate at least one of radio-frequency electromagnetic fields and microwave-frequency electromagnetic fields.

B12. The apparatus of any of paragraphs B1-B11.3, further comprising the test coupon clamped to the cantilever support and in contact with the cell.

B12.1. The apparatus of paragraph B12, wherein the test coupon serves as a working electrode to the counter electrode.

B12.2. The apparatus of any of paragraphs B12-B12.1, wherein the test coupon includes a substrate.

B12.2.1. The apparatus of paragraph B12.2, wherein the test coupon includes a coating on the substrate, that is between the substrate and the counter electrode. 812.2.1.1. The apparatus of paragraph B12.2.1, wherein the coating forms a dielectric barrier over the substrate in the test region.

B12.2.1.2. The apparatus of any of paragraphs B12.2.1-612.2.1.1, wherein the coating is at least one of a non-conductive coating, an insulative coating, and a dielectric coating.

B12.2.2. The apparatus of any of paragraphs B12.2-612.2.1.2, wherein the substrate is at least one of a conductive substrate and a metal substrate.

B12.2.3. The apparatus of any of paragraphs B12.2-612.2.2, wherein the substrate serves as a working electrode to the counter electrode.

B12.3. The apparatus of any of paragraphs B12-612.2.3, wherein the test coupon includes an electrode that serves as a working electrode to the counter electrode.

B12.4. The apparatus of any of paragraphs B12-B12.3, wherein the test coupon is at least one of a panel, a sheet, and a laminate.

B13. The apparatus of any of paragraphs B1-B12.4, further comprising a seal at a base of the cell that is configured to contact the test coupon and to fluidically seal the cell to the test coupon.

B14. The apparatus of any of paragraphs B1-B13, further comprising a controller configured to measure at least one of voltage and electrical current with the electrical meter, configured to operate the force application mechanism to apply mechanical loads to the test coupon, and programmed to perform the method of any of paragraphs A1-A22.

B15. The method of any of paragraphs A1-A22 performed with the apparatus of any of paragraphs B1-B14.

B16. The use of the apparatus of any of paragraphs B1-B14 to perform the method of any of paragraphs A1-A22.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the phrase, "for example," the phrase, "as an example," and/or simply the term "example," when used with reference to one or more components, features, details, structures, examples, and/or methods according to the present disclosure, are intended to convey that the described component, feature, detail, structure, example, and/or method is an illustrative, non-exclusive example of components, features, details, structures, examples, and/or methods according to the present disclosure. Thus, the described component, feature, detail, structure, example, and/or method is not intended to be limiting, required, or exclusive/exhaustive; and other components, features, details, structures, examples, and/or methods, including structurally and/or functionally similar and/or equivalent components, features, details, structures, examples, and/or methods, are also within the scope of the present disclosure.

As used herein, the phrases "at least one of" and "one or more of," in reference to a list of more than one entity, means any one or more of the entities in the list of entities, and is not limited to at least one of each and every entity specifically listed within the list of entities. For example, "at least one of A and B" (or, equivalently, "at least one of A or B," or, equivalently, "at least one of A and/or B") may refer to A alone, B alone, or the combination of A and B.

As used herein, the singular forms "a", "an" and "the" may be intended to include the plural forms as well, unless the context clearly indicates otherwise.

The various disclosed elements of systems and steps of methods disclosed herein are not required of all systems and methods according to the present disclosure, and the present disclosure includes all novel and non-obvious combinations and subcombinations of the various elements and steps disclosed herein. Moreover, any of the various elements and steps, or any combination of the various elements and/or steps, disclosed herein may define independent inventive subject matter that is separate and apart from the whole of a disclosed system or method. Accordingly, such inventive subject matter is not required to be associated with the specific systems and methods that are expressly disclosed herein, and such inventive subject matter may find utility in systems and/or methods that are not expressly disclosed herein.

The invention claimed is:

1. A method of determining an electrochemical response of a test coupon, the method comprising:
   clamping the test coupon in a cantilevered arrangement with a clamped end of the test coupon clamped to a cantilever support and a free end of the test coupon distal to the clamped end;
   applying an electrolyte solution to a test region on the test coupon;
   contacting the electrolyte solution with a counter electrode;
   applying a mechanical load to the test coupon to produce a deflection event, wherein the applying the mechanical load includes inducing a dampened oscillatory motion of the test region;
   before applying the mechanical load, measuring a pre-event value of an electrical parameter of the test coupon;
   after applying the mechanical load, measuring a post-event value of the electrical parameter; and
   determining an electrochemical response of the test coupon to the mechanical load based on the post-event value and the pre-event value.

2. The method of claim 1, wherein the applying the mechanical load includes applying the mechanical load to a contact site at the free end of the test coupon.

3. The method of claim 1, wherein the deflection event includes an application phase while the mechanical load is applied and a release phase after the mechanical load is removed.

4. The method of claim 1, further comprising repeatedly applying the mechanical load and then measuring the post-event value after applying the mechanical load.

5. The method of claim 4, wherein the applying the mechanical load and the measuring the post-event value are performed synchronously.

6. The method of claim 1, wherein the electrical parameter includes at least one of capacitance between the counter electrode and the test coupon, resistance between the counter electrode and the test coupon, impedance between the counter electrode and the test coupon, capacitance of the test coupon in the test region, resistance of the test coupon in the test region, impedance of the test coupon in the test region, and open-circuit potential between the counter electrode and the test coupon in the test region.

7. The method of claim 1, wherein the applying the electrolyte solution includes flexibly sealing a cell of the electrolyte solution to the test coupon about the test region.

8. The method of claim 7, wherein the test coupon includes a substrate and a coating covering at least a portion of the substrate, and wherein the applying the electrolyte solution includes sealing the cell to the coating.

9. The method of claim 1, further comprising vibrationally isolating the test coupon from external vibrational energy.

10. The method of claim 1, further comprising electrically isolating the test coupon from external electromagnetic fields.

11. A method of assessing corrosion protection performance of a coating on a metal substrate, the method comprising:
    clamping a test coupon, which includes the coating on the metal substrate, in a cantilevered arrangement with a clamped end of the test coupon clamped to a cantilever support and a free end of the test coupon distal to the clamped end;
    applying an electrolyte solution to a test region on the test coupon;

contacting the electrolyte solution with a counter electrode and a reference electrode;

applying a mechanical load to the test coupon to produce a deflection event, wherein the applying the mechanical load includes inducing a dampened oscillatory motion of the test region;

before applying the mechanical load, measuring a pre-event value of an electrical parameter of the test coupon with at least one of the counter electrode and the reference electrode;

after applying the mechanical load, measuring a post-event value of the electrical parameter with at least one of the counter electrode and the reference electrode; and determining a corrosion performance indicator of the coating on the metal substrate based on the pre-event value and the post-event value, wherein the corrosion performance indicator includes at least one of a difference of and a ratio of the pre-event value and the post-event value.

12. The method of claim 11, wherein the electrical parameter includes at least one of capacitance between the counter electrode and the test coupon and capacitance of the test coupon in the test region.

13. The method of claim 11, wherein the electrical parameter includes at least one of an open-circuit potential between the counter electrode and the test coupon in the test region, and an open-circuit potential between the reference electrode and the test coupon in the test region.

14. The method of claim 11, wherein the applying the electrolyte solution includes flexibly sealing a cell of the electrolyte solution to the test coupon about the test region.

15. An apparatus for measuring corrosion protection performance, the apparatus comprising:

a cantilever support configured to support a test coupon at a clamped end and in a cantilevered arrangement such that a free end of the test coupon is distal the clamped end;

a counter electrode;

a reference electrode;

a cell configured to hold an electrolyte solution in contact with a test region of the test coupon, wherein the counter electrode is configured to electrically contact the test coupon via the cell containing the electrolyte solution, and wherein the reference electrode is configured to electrically contact the test coupon and the counter electrode via the cell containing the electrolyte solution;

a force application mechanism configured to apply a mechanical load to the test coupon at the free end, wherein the force application mechanism is configured to apply to the test coupon a repeated force that includes an application phase while the mechanical load is applied to the test coupon and a release phase after the mechanical load is removed from the test coupon; and an electrical meter configured to measure at least one of voltage and electrical current at the test coupon.

16. The apparatus of claim 15, wherein the force application mechanism includes one or more of a striker, a hammer, a tooth, a prong, and an actuator.

17. The method of claim 1, wherein the applying the mechanical load includes implying an impulsive mechanical load.

18. A method of determining an electrochemical response of a test coupon, the method comprising:

clamping the test coupon in a cantilevered arrangement with a clamped end of the test coupon clamped to a cantilever support and a free end of the test coupon distal to the clamped end;

applying an electrolyte solution to a test region on the test coupon;

contacting the electrolyte solution with a counter electrode;

applying a mechanical load to the test coupon to produce a deflection event, wherein the deflection event includes an application phase while the mechanical load is applied and a release phase after the mechanical load is removed;

before applying the mechanical load, measuring a pre-event value of an electrical parameter of the test coupon;

after applying the mechanical load, measuring a post-event value of the electrical parameter; and determining an electrochemical response of the test coupon to the mechanical load based on the post-event value and the pre-event value.

* * * * *